United States Patent [19]
Luderer et al.

[11] Patent Number: 5,912,135
[45] Date of Patent: *Jun. 15, 1999

[54] METHODS FOR DIAGNOSING BENIGN PROSTATIC DISEASES

[76] Inventors: Albert A. Luderer, 28 Catbrier Rd., Weston, Conn. 06883; Grant D. Carlson, 460 Clark La., Orange, Conn. 06477; Robert P. Thiel, 789 Litchfield Turnpike, Bethany, Conn. 06524; Thomas F. Soriano, 2 Benz St., Ansonia, Conn. 06524; William J. Kramp, 1061 Johnson Rd., Woodbridge, Conn. 06525

[ * ] Notice: This patent is subject to a terminal disclaimer.

[21] Appl. No.: 08/604,685

[22] Filed: Feb. 21, 1996

Related U.S. Application Data

[63] Continuation-in-part of application No. 08/393,214, Feb. 23, 1995, Pat. No. 5,698,402.

[51] Int. Cl.⁶ .................................................. G01N 33/573
[52] U.S. Cl. ........................... 435/7.4; 435/7.94; 436/64; 436/86
[58] Field of Search ................................... 435/7.4, 7.94; 436/64, 86

[56] References Cited

PUBLICATIONS

W.J. Catalona et al, Jour. Amer. Med. Assoc., 274, 1214–1220, 1995.
A. Christensson et al, Jour. Urol., 150, 100–105, 1993.
A.A. Luderer et al, Urology, 46, 187–194, 1995.
K. Mitrunen et al, Clin. Chem; 41, 1115–1120, 1995.
J.E. Osterling et al, Urol. Clin. North. Amer., 20, 671–680, 1993.

*Primary Examiner*—David Saunders
*Attorney, Agent, or Firm*—Brian D. Voyce

[57] ABSTRACT

The present invention relates to novel methods for diagnosing benign prostatic diseases (BPD), such as benign prostatic hyperplasia, prostatitis, or glandular atrophy, in a male human patient without requiring a biopsy. The total prostate specific antigen (PSA) level in the blood or serum of the patient is measured. If the patient has a total PSA level of between about 2.5 ng/ml and 10.0 ng/ml, then the free PSA level in the blood or serum of the patient is measured. The proportion of free PSA to total PSA is calculated. If this proportion is equal to or greater than about 25%, then the patient is diagnosed as having BPD. Optionally, if the patient has a total PSA level of between 10.1 ng/ml and 20.0 ng/ml, then the free PSA level in the blood or serum of the patient can also be measured. The proportion of free PSA to total PSA is calculated. If this proportion is equal to or greater than about 25%, then the patient is diagnosed as having BPD.

3 Claims, 7 Drawing Sheets

| DIAGNOSTIC REPORT | PATIENT: _________ | |
|---|---|---|
| TOTAL PSA | F/T RATIO | DIAGNOSIS |
| 5.0 ng/ml | > 45% | BPH |

METHODS FOR DIAGNOSING BENIGN PROSTATIC DISEASES

The present application is a continuation-in-part of Ser. No. 393,214, filed Feb. 23, 1995, which has issued as U.S. Pat. No. 5,698,402.

TECHNICAL FIELD

The present invention relates to novel methods for diagnosing benign prostatic diseases (BPD), such as benign prostatic hyperplasia, prostatitis, or glandular atrophy, in a male human patient without requiring a biopsy. The total prostate specific antigen (PSA) level in the blood or serum of the patient is measured. If the patient has a total PSA level of between 2.5 ng/ml and 10.0 ng/ml, then the free PSA level in the blood or serum of the patient is measured. The proportion of free PSA to total PSA is calculated. If this proportion is equal to or greater than about 25%, then the patient is diagnosed as having BPD. Optionally, if the patient has a total PSA level of between 10.1 ng/ml and 20.0 ng/ml, then the free PSA level in the blood or serum of the patient can also be measured. The proportion of free PSA to total PSA is calculated. If this proportion is equal to or greater than about 25%, then the patient is diagnosed as having BPD.

BACKGROUND ART

Prostate specific antigen (PSA) is recognized as a molecular marker for prostatic adenocarcinoma (CAP). Blood or serum based immunoassays measuring the total PSA level have been commercially available for a number of years. However, the detection of total PSA does not necessarily mean that a patient has CAP. In order to distinguish CAP, a total PSA test has to satisfy two elements: a high sensitivity—the ability to detect disease when present, and a high specificity—the ability to detect true negatives and avoid false positives. From clinical experience, total PSA tests have become generally accepted as being predictive of CAP if the total PSA level is greater than 10.0 ng/ml. Total PSA values between 0.0 ng/ml and about 3.9 ng/ml have been considered generally predictive of no disease being present, with a value of about 3.5 ng/ml being used for men under 60 years old and about 2.5 ng/ml being used for men under 50 years old. (See Oesterling, J. E., Cooner, W. H., Jacobsen, S. J., Guess H. A., and Lieber, M. M.: *"Influence of Patient Age on the Serum PSA Concentration and Important Clinical Observations"*: Urol. Clin. North Am.; Vol. 20: 671–680, 1993.)

PSA is primary organ-specific, not cancer specific. Thus, PSA in blood or serum can result not only from CAP, but also from normal or hyperplastic prostate tissues. Historically, a total PSA test cannot reliably distinguish BPD from CAP at less than 10.0 ng/ml. Studies have found that 43% (136/319) of patients with organ-confined CAP have a total PSA value within the normal range of less than 4.0 ng/ml. Moreover, about 25% (148/597) of men with BPD have a total PSA value above 4.0 ng/ml. (See Oestering, J. E.: *"Prostate Specific Antigen: A Critical Assessment of the Most Useful Tumor Marker for Adenocarcinoma of the Prostate"*, J. Urol., Vol:145: 907–923, 1991.) Standard medical practice is to biopsy patents over 60 years old having total PSA levels of between 4.0 ng/ml and 10.0 ng/ml because about 30% of those patients have CAP. Likewise, patients between 50 years and 60 years old whose total PSA falls between 3.5 ng/ml and 10.0 ng/ml and patients under 50 years old whose total PSA falls between 2.5 ng/ml and 10.0 ng/ml are also biopsied under current medical practice.

One proposed method for detecting CAP is disclosed in Serial Number WO 92/01936 to Hans Lilja et al., (Lilja application), filed Jul. 22, 1991, under the Patent Cooperation Treaty (PCT). In general, the Lilja application discloses using immunoassays to measure free PSA and a complexed form of PSA. Free PSA is a 33 kDa single chain glycoenzyme that is produced by the epithelial cells lining the acini and prostatic ducts of the prostate gland. Complexed PSA refers primarily to a 90 kDa complex of PSA bound to alpha 1- antichymotrypsin (ACT) protein. Free PSA and complexed PSA, and their proportions are applied in the diagnosis of patients with CAP. Throughout, the specification discloses using a combination of a free PSA to total PSA (F/T) proportion and a complexed PSA to total PSA (C/T) proportion for use in diagnosing CAP. No prostate needle biopsy were performed on the patients, and the patients covered a full range of total PSA values. The text provides no guidance as to specifically how one uses these proportions.

DISCLOSURE OF THE INVENTION

The present invention relates to a method for diagnosing BPD in a male human patient without requiring a biopsy. Presently, if a patient has a total PSA level of 4.0 ng/ml to 10.0 ng/ml, then he is considered to be in a "gray" diagnostic zone and must undergo a prostate needle biopsy, an anesthetic-free operation performed transrectally involving substantial pain and discomfort, especially if a sextant biopsy is performed which requires tailing six samples. The present method eliminates the need for about one-third of those patients to undergo such a biopsy. (See Luderer, A. A., et alia, *"Measurement of the Proportion of Free to Total Prostate-Specific Antigen Improves Diagnostic Performance of Prostate-Specific Antigen in The Diagnostic Gray Zone of Total Prostate-Specific Antigen"*, Urol., Vol. 46: 187–194, 1995.)

In an embodiment for those patients in the gray diagnostic zone, the method comprises four steps. First, one measures the total PSA level in the blood or serum of the patient. Second, one measures the free PSA level in the blood or serum of a patient, but only if he has a total PSA level of between about 2.5 ng/ml and about 10.0 ng/ml. If the patient has a total PSA level below 2.5 ng/ml then he is diagnosed to have BPD. If the patient has a total PSA level above 10.0 ng/ml then he is presumed to have CAP and must be biopsied. Third, one calculates the proportion of free PSA to total PSA. Fourth and finally, one diagnoses the patient as having BPD if the calculated proportion of free PSA to total PSA is equal to or greater than about 25%. Optionally, if the patient is between 50 years old and under 60 years old, one can use a lower cutoff level of 3.5 ng/ml, and if the patient is at least 60 years old, then one can perform the same steps using a lower cutoff level of 4.0 ng/ml.

A report for a diagnosis of BPD in a male human patient without requiring a biopsy according to the above embodiment comprises listing a total PSA level of between 2.5 ng/ml, (optionally 3.5 ng/ml for those between 50 years old and under 60 years old, and 4.0 ng/ml for those at least 60 years old), and 10.0 ng/ml and listing a free PSA to total PSA proportion equal to or greater than about 25%.

The present invention also relates to a method for diagnosing BPD in a male human patient who traditionally was assumed to have CAP, i.e., patients having a total PSA level of 10.1 ng/ml to 20.0 ng/ml. Unlike in the past these patients can be screened and identified as having BPD, rather than CAP. In this second embodiment, the present method also comprises four steps. First one measures the total PSA level in the blood or serum of the patient. Second, one measures the free PSA level in the blood or serum of a patient. Third, one calculates the proportion of free PSA to total PSA. Fourth and finally, one diagnoses the patient as having BPD if the calculated proportion of free PSA to total PSA is equal to or greater than about 25%. The physician can use this method either with or without performing a transrectal biopsy. While the standard of care in a particular region may initially dictate that a physician perform such biopsies, the present method does not require one in order to be effective in diagnosing patients with BPD.

A report for a diagnosis of BPD in these higher total PSA patients comprises listing a total PSA level of between about 10.0 ng/ml and about 20.0 ng/ml and listing a free PSA to total PSA proportion equal to or greater than about 25%.

Thus, the present methods allow the physician to diagnose BPD in patients having a total PSA level extending from about 2.5 ng/ml up to 20.0 ng/ml.

BEST MODES FOR CARRYING OUT THE INVENTION

Assays

Figure 1:
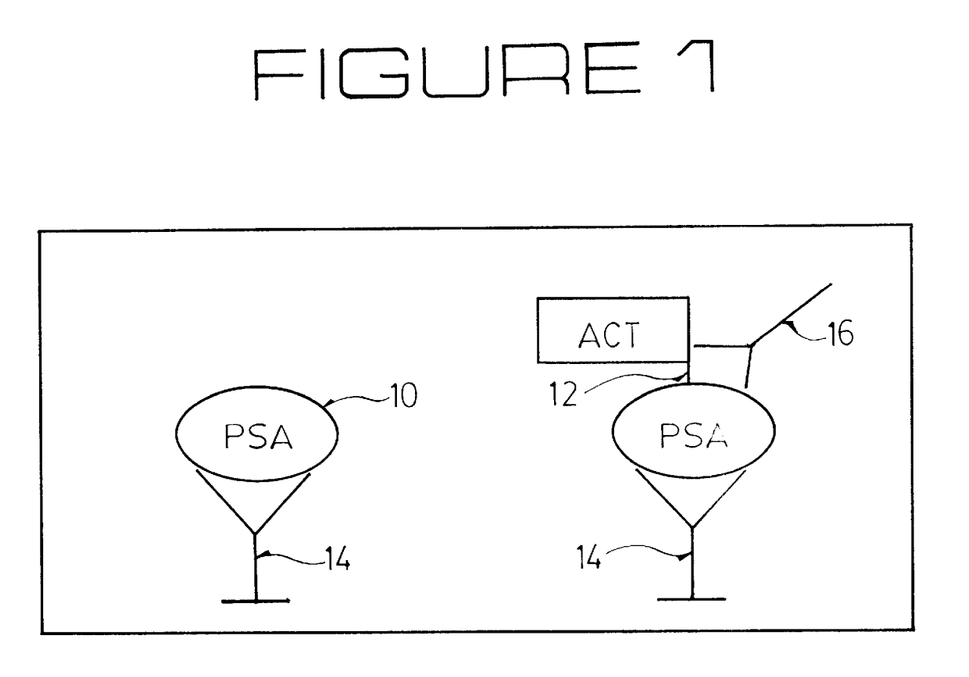
FIG. 1 is a diagrammatic view of the total PSA assay used in the present invention.

In preferred embodiments described below, the present method uses two immunoassays, however any specific binding assay that measures either free PSA or total PSA is suitable for the present methods. The first assay is a total PSA sandwich immunoassay manufactured by Tosoh Medics, Inc. (Tosoh) of Foster City, Calif. The assay is an immunoenzymetric assay using dual murine monoclonal antibodies. FIG. 1 shows diagrammatically how, in the final sandwich configurations, this first assay captures both free PSA (10) and complexed PSA/ACT (12) using a capture antibody (14) and an enzyme labeled antibody (16).

Figure 2:
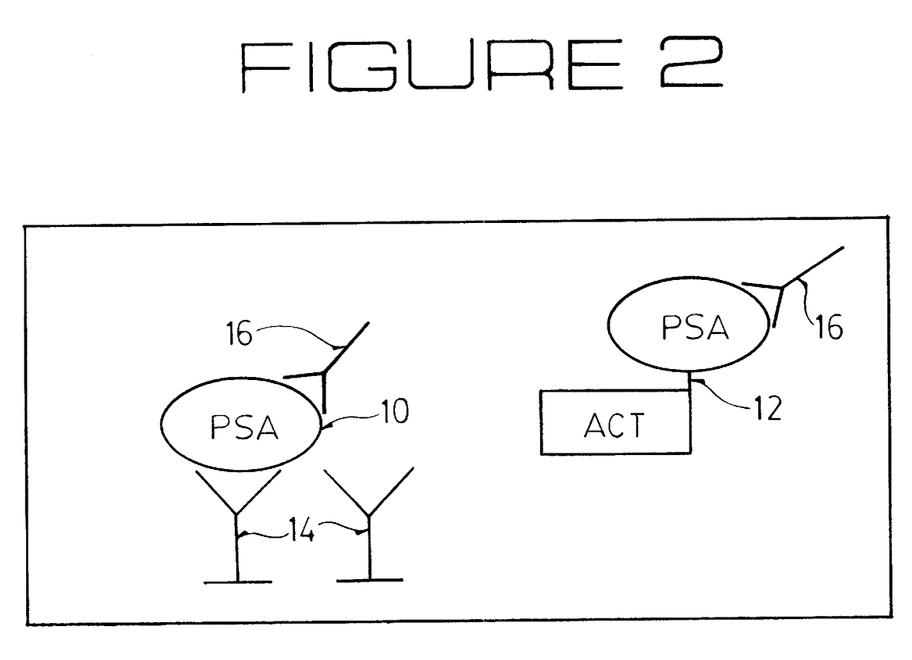
FIG. 2 is a diagrammatic view of the free PSA assay used in the present invention.

The second assay is a free PSA immunoassay manufactured developed by Immuno Corp. for Dianon Systems, Inc. (Dianon) of Stratford, Conn. This free PSA test is designed to detect free PSA in serum using an IRMA coated tube format. Free PSA binds to a tube coated by a monoclonal antibody which selectively binds free PSA but not complexed PSA. After washing, an $I^{125}$ labeled polyclonal antibody against free PSA is reacted with the bound free PSA. The physician is given a result that expresses a proportion of free PSA to total PSA. FIG. 2 shows diagrammatically how in the final sandwich configuration, this second assay captures free PSA (10), but the capture antibody (14) does not specifically bind to the complex of the PSA/ACT complex (12) and radiolabelled antibody (16).

Example 1

Lower Total PSA Patient

In a clinical study to validate the present invention, 434 patients were tested. Classified as "normals", 96 males were identified as being between 45 years and 75 years old and having a normal PSA (i.e., less than 2.5 ng/ml total PSA if under 60 years old and less than 4.0 if over 60 years old), a normal digital rectal examination (DRE), and no history of CAP. The age mean was 57. Classified as "BPD", 222 males were identified as being between 45 years old and 75 years old, having BPD histologically confined by sextant needle prostate biopsy, and no history of cancer. The age mean was 65. Classified as "CAP", 116 males were identified as being between 45 years old and 75 years old and having primary CAP histologically confirmed by needle prostate biopsy. The age mean was 66. None of the above patients received any form of prostate-related treatment prior to blood draw. Total PSA was measured using the Tosoh assay described above, in accordance with the manufacturer's instructions. Free PSA was measured using the Dianon assay described above, in accordance with the manufacturer's instructions.

If one restricts the patient population to those 111 CAP patients and 222 BPD patients having a total PSA range of between 2.5 ng/ml to 10.0 ng/ml, the use of a total PSA blood or serum test alone does not provide any ability to distinguish clinically between CAP patients or BPD patients.

TABLE 1

|  | CAP | BPD |
|---|---|---|
| Mean | 6.3 | 5.9 |
| Median | 6.1 | 5.6 |
| 95% Confidence level for Mean | (5.91–6.69) | (5.70–6.10) |

(There is no statistically relevant difference in these results.)

While the addition of the step of measuring free PSA and the calculation of a free PSA to total PSA proportion did produce a marked clinical delineation between the mean values for CAP patients and the others, in the suspect group having a total PSA level of between 2.5 ng/ml and 10.0 ng/ml there was no use for the mean values alone as a diagnostic modality.

TABLE 2

|  | CAP | BPD |
|---|---|---|
| Mean(F/T%) | 14.5 | 20.5 |
| Median(F/T%) | 13.0 | 18.5 |
| 95% Conf. level for Mean(%) | (13.3–15.7) | (18.3–21.7) |

However, if the patients are restricted to those having a total PSA of from about 2.5 ng/ml to about 10.0 ng/ml, and sensitivity/specificity relationships are examined with respect to F/T proportions, then significantly different results are obtained. One can differentiate certain BPD patients with great certainty using a F/T proportion cutoff of greater than about 25%. The following table shows the relationship between F/T proportion and sensitivity/specificity:

TABLE 3

| F/T PSA Proportion | Sensitivity | Specificity |
|---|---|---|
| <7% | 11% | 98% |
| <10% | 30% | 92% |
| <12% | 43% | 84% |
| <15% | 66% | 69% |
| <20% | 88% | 47% |
| <25% | 96% | 22% |
| <30% | 97% | 13% |

(Here, sensitivity is reported with respect to CAP, thus at an F/T proportion of <25%, the 96% figure means that essentially all CAP patients are present. Conversely, at an F/T proportion of >25% essentially no CAP patients, only BPD patients are present.)

By using the about 25% F/T proportion level as a cutoff point for patients having a total PSA of between 2.5 ng/ml and 10.0 ng/ml, one can diagnose a patient pool that is essentially all patients having BPD. These patients can forego an invasive and painful transrectal needle biopsy.

Figure 3:
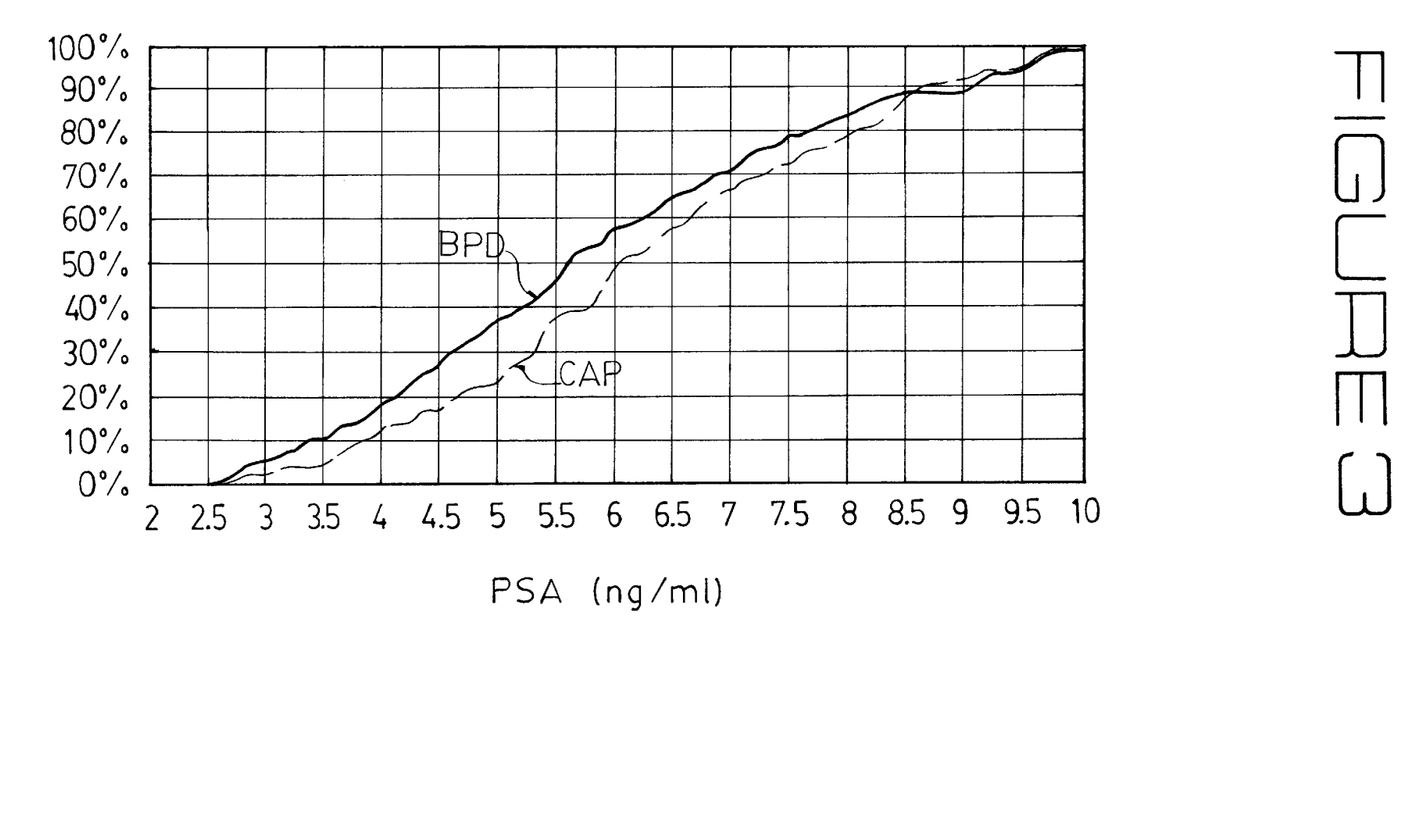
FIG. 3 is a graph showing the distribution of total PSA levels for BPD, patients and CAP patients in Example 1.
Figure 5:
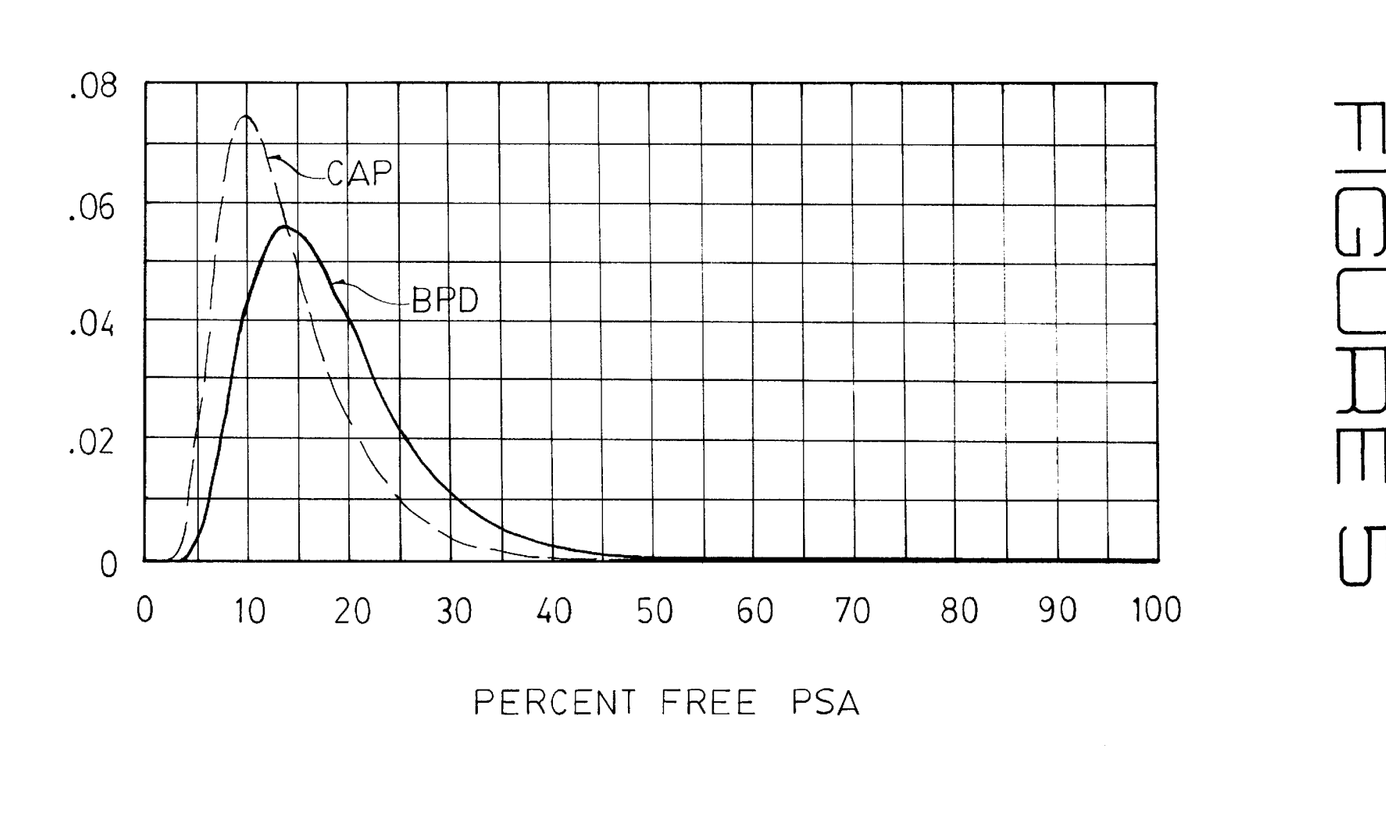
FIG. 5 is a graph showing the distribution of F/T proportions for BPD patients and CAP patients in Example 1.

Graphic evidence of the discriminating power of the present method can be found in FIGS. 3 and 5. FIG. 3 shows the cumulative percent distribution of the total PSA blood or serum levels in patients within the select total PSA range of about 2.5 ng/ml and 10.0 ng/ml. One can easily see the minimal separation between the CAP patients and the BPD patients. FIG. 5 shows the distribution of patients having CAP or BPD in relation to the F/T PSA proportion in the blood or serum levels of patients within the select total PSA range of 2.5 ng/ml to 10.0 ng/ml. Clearly the CAP patients can be separated from certain BPD patients by using the about 25% mark.

Using the present method, and in view of the above clinical data, one can expect the following scenario if 1000 patients are screened, each having the requisite minimum total PSA. A total of 250 patients will have CAP. Of those, 96% will have a F/T proportion less than about 25%. The bulk of the 1000 patients (750) will have BPD. Of those, 78%, or 585 patients, will have a F/T proportion less than about 25%. The remaining 22% of the BPD patients will have a F/T proportion greater than about 25%. By using the present method to diagnose BPD, virtually none of the patients having CAP and a total PSA of between 2.5 ng/ml and 10.0 ng/ml will escape detection. Moreover, about one-third of the BPD patients would be prevented from having to undergo a painful transrectal biopsy.

In a time of increasing concern about health care costs and unnecessary medical procedures, the present method provides a powerful cost-saving clinical tool to the urologist. Patients can be put at ease who in the past had to be told that there was a concern of cancer being present but no proof. Using the present method, about one quarter of the patients do not need biopsies. Moreover, about one-third of the patients biopsied will have CAP, a substantial enrichment from current practice.

Figure 4:
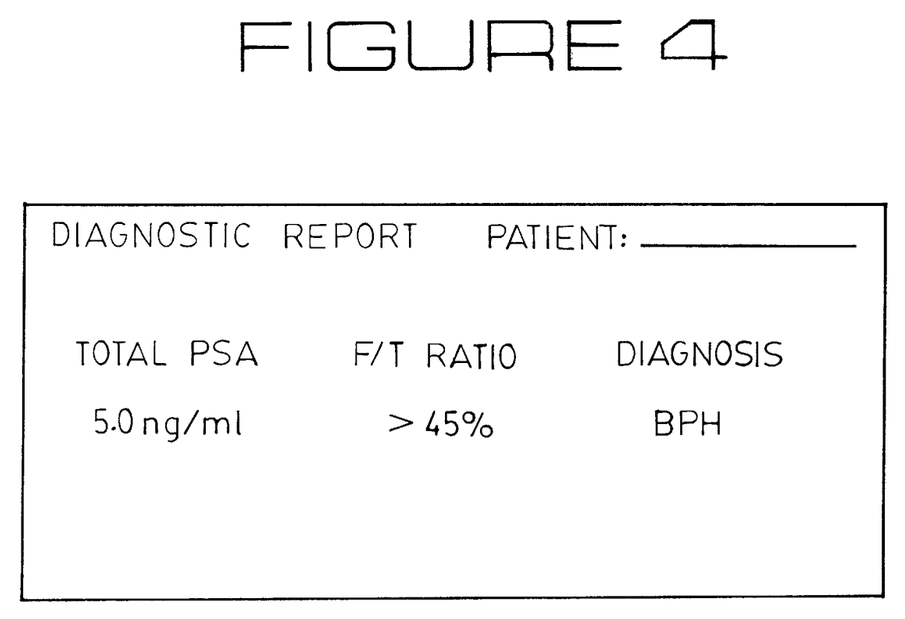
FIG. 4 is a view of a pathology report according to the present invention.

FIG. 4 illustrates a pathology report that uses the present method. The report includes a listing of the results of a first assay for total PSA. The total PSA level for the patient is between 2.5 ng/ml and 10 ng/ml. It also includes a listing of a calculation occurring from a free PSA assay—the free PSA to total PSA proportion. The F/T proportion is equal to or greater than about 25%. Finally, the report includes a diagnosis of the patient having BPD.

Example 2

Higher Total PSA Patients

In a clinical study to validate the present invention for patients traditionally diagnosed as having CAP, 186 patients were tested. Classified as "normals", 96 males were identified as being between 45 years and 75 years old and having a normal PSA (i.e., less than 2.5 ng/ml total PSA if under 60 years old and less than 4.0 if over 60 years old), a normal digital rectal examination (DRE), and no history of CAP. The age mean was 57. Classified as "BPD", 41 males were identified as being between 45 years old and 75 years old, having benign prostate disease histologically confirmed by sextant needle prostate biopsy, and no history of cancer, even though they each had a total PSA blood level of between 10.1 ng/ml and 20.0 ng/ml. The age mean was 66. Classified as "CAP", 49 males were identified as being between 45 years old and 75 years old, having a total PSA level of between 10.1 ng/ml and 20.0 ng/ml, and having primary CAP histologically confirmed by needle prostate biopsy. The age mean was 68. None of the above patients received any form of prostate-related treatment prior to blood draw. Total PSA was measured using the Tosoh assay described above, in accordance with the manufacturer's instructions. Free PSA was measured using the Dianon assay descried above, in accordance with the manufacturer's instructions.

Table 4 outlines the results of total PSA testing for patients in the 10.1 ng/ml to 20.0 ng/ml range.

TABLE 4

| STATUS | CAP | BENIGN |
|---|---|---|
| (Total PSA level) | All ages | |
| Mean | 13.8 | 12.9 |
| Median | 14.0 | 12.0 |
| Std. Dev. | 2.1 | 2.6 |
| 95% CL for mean | (13.2–14.4) | (12.1–13.2) |

(There is no statistically relevant difference in these results.)

As can be seen from this data, total PSA testing does not discriminate between CAP and BPD in the 10.1 ng/ml to 20.0 ng/ml range Table 5 outlines the results of free PSA to total PSA testing for the patients in Table 4.

TABLE 5

|  | CAP | BPD |
|---|---|---|
| Mean(F/T%) | 12.9 | 21.0 |
| Median(F/T%) | 11.0 | 19.0 |
| 95% Conf. level for Mean(%) | (11.3–14.5) | (17.9–24.1) |

For patients having a total PSA level of between 10.1 ng/ml and 20.0 ng/ml, Table 5 shows that the addition of calculating the F/T PSA proportion does not indicate how to differentiate between all patients having CAP and those having BPD, as traditionally believed by practicing physicians. However, if sensitivity/specificity relationships are examined with respect to F/T proportions, then significantly different results are observed. One can differentiate certain BPD patients with great certainty using a F/T proportion cutoff of greater than about 25%, even among patients traditionally believed to have CAP. The following table shows the relationship between F/T proportion and sensitivity/specificity:

TABLE 6

| F/T PSA Proportion | Sensitivity | Specificity |
|---|---|---|
| <7% | 20% | 98% |
| <10% | 45% | 88% |
| <12% | 57% | 80% |
| <15% | 69% | 59% |
| <20% | 90% | 44% |
| <25% | 98% | 29% |
| <30% | 100% | 22% |

(Here, sensitivity is reported with respect to CAP, thus at an F/T proportion of <25%, the 100% figure means that all CAP patients are present. Conversely, at an F/T proportion of >25% essentially no CAP patients, only BPD patients are present.)

By using the about 25% F/T proportion level as a cutoff point for patients having a total PSA of between about 10.0 ng/ml and 20.0 ng/ml, one can diagnose a patient pool that is essentially all patients having BPD. These patients can forego an invasive and pain transrectal needle biopsy, or if they have already undergone one and have a negative biopsy, may be considered as CAP-free.

Figure 6:
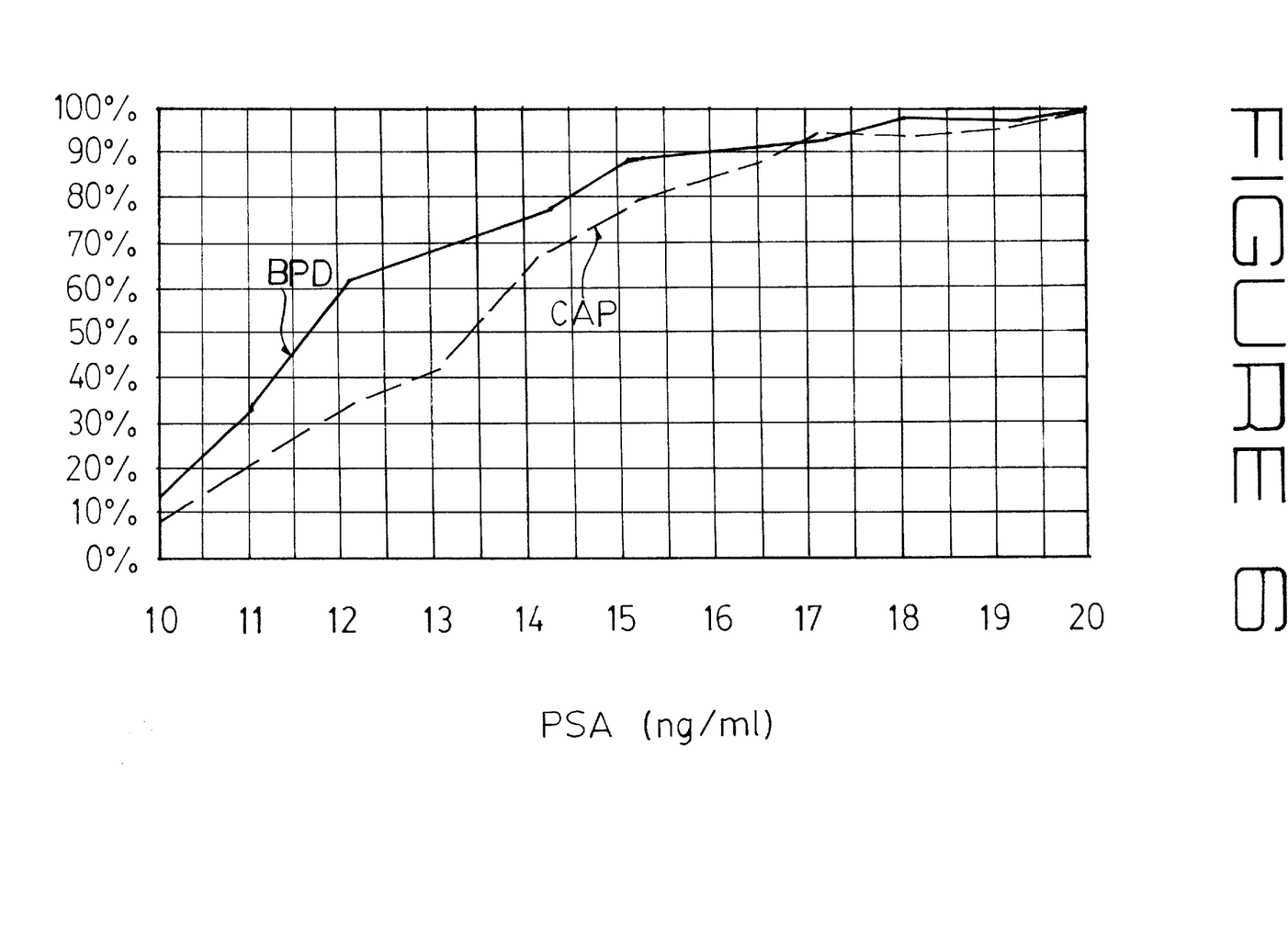
FIG. 6 is a graph showing the cumulative percent distribution of total PSA levels for BPD patients and CAP patients in Example 2.
Figure 7:
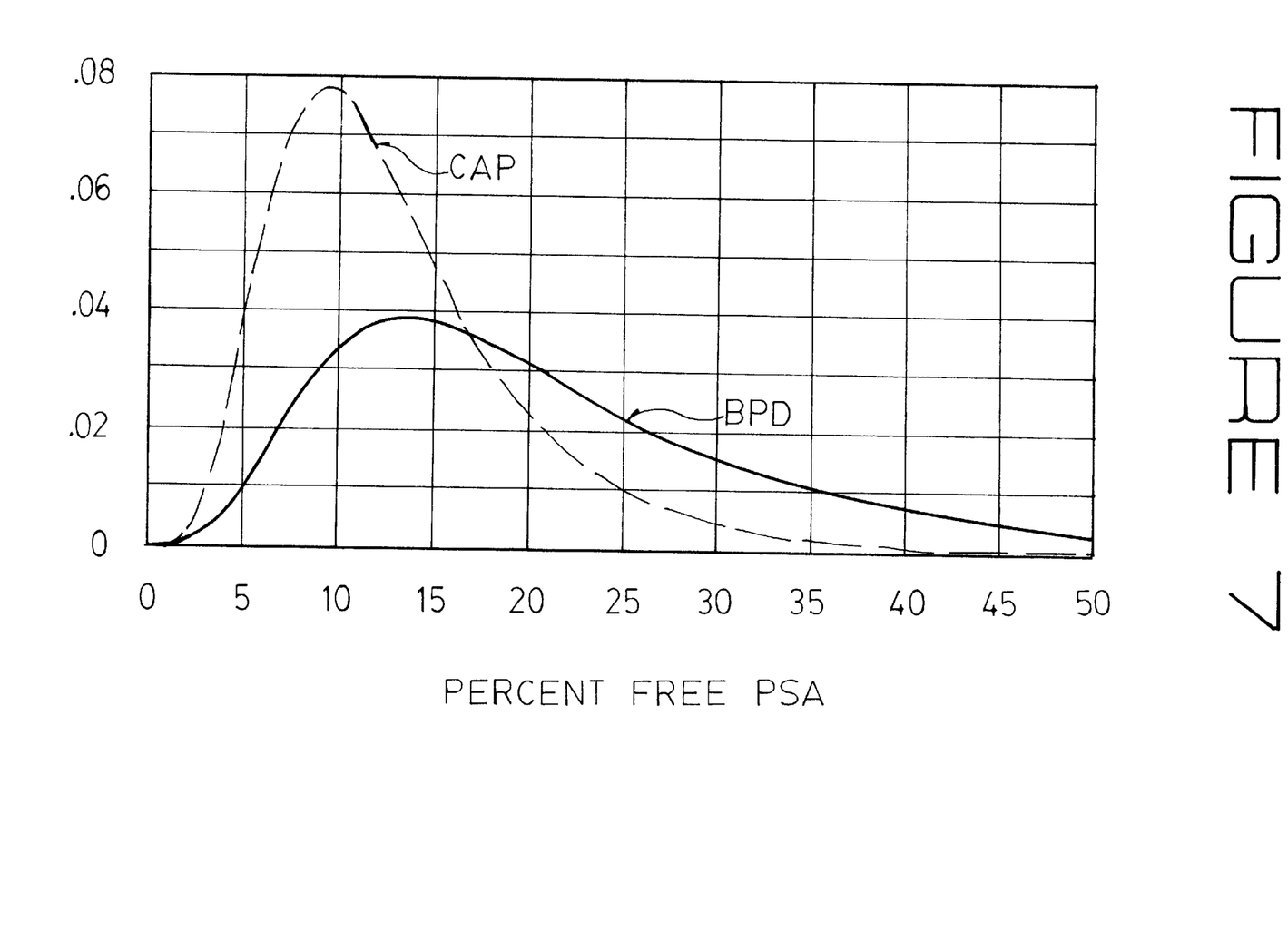
FIG. 7 is a graph showing the cumulative percent distribution of F/T proportions for BPD patients and CAP patients in Example 2.

Graphic evidence of the discriminating power of the present method can be found in FIGS. 6 and 7. FIG. 6 shows the cumulative percent distribution of patients having CAP or BPD in relation to the total PSA blood or serum levels of patients within the select total PSA range of 10.1 ng/ml to 20.0 ng/ml. One notices the poor discrimination between the CAP patients and the BPD patients. FIG. 7 shows the distribution of patients having CAP or BPD in relation to the F/T PSA proportion in the blood or serum levels of patients within the select total PSA range of 10.1 ng/ml to 20.0 ng/ml. One can easily see the separation between the CAP patients and the BPD patients.

Using the present method, and in view of the above clinical data, one can expect the following scenario if 1000 patients are screened, each having the requisite minimum total PSA. A total of 500 patients will have CAP. Of those, 98% will have a F/T proportion less than about 25%. The bulk of the remaining 500 patients will have BPD. Of those, 71%, or 355 patients, will have a F/T proportion less than about 25%. The remaining 29% of the BPD patients will have a F/T proportion greater than about 25%. By using the present method to diagnose BPD, virtual none of the patients having CAP and a total PSA of between 10.1 ng/ml and 20.0 ng/ml will escape detection. Moreover, about 145 of the BPD patients can be prevented from having to undergo a painful transrectal biopsy.

In a time of increasing concern about health care costs and unnecessary medical procedures, the present method provides a powerful cost-saving clinical tool to the urologist and can be of great comfort to the patient. Patients having a total PSA level of from 10.1 ng/ml to 20.0 ng/ml can be diagnosed as not having CAP, whereas in the past they were assumed to have cancer. Using the present method, about 15% of the patients do not require biopsies. Moreover, about 60% of the patients biopsied will have CAP, a substantial enrichment from current practice.

All publications or unpublished patent applications mentioned herein are hereby incorporated by reference thereto.

Other embodiments of the present invention are not presented here which are obvious to those of skill in the art, now or during the term of any patent issuing herefrom, and thus, are within the spirit and scope of the present invention.

We claim:

1. A method for diagnosing benign prostatic hyperplasia (BPH) in a male human patient comprising:

a) measuring the total prostate specific antigen (PSA) level in the blood or serum of the patient;

b) measuring the free PSA level in the blood or serum of the patient only if the patient has a total PSA level of between above 10.1 ng/ml and about 20.0 ng/ml;

c) calculating the proportion of free PSA to total PSA; and d) diagnosing the patient as having BPH if the calculated proportion of free PSA to total PSA is equal to or greater than about 25%.

2. The method of claim 1 wherein the patient also has a negative prostate biopsy.

3. A method for differentiating between benign prostatic hyperplasia and prostatic adenocarcinoma comprising:

a) measuring the total prostate specific antigen (PSA) level in the blood or serum of a patient;

b) measuring the free PSA level in the blood or serum of the patient only if the patient has a total PSA level of between 2.5 ng/ml, if the patient is under 60 years old, or 4.0 ng/ml, if the patient is at least 60 years old, and 10.0 ng/ml;

c) calculating the proportion of free PSA to total PSA; and d) differentiating the patient as having benign prostatic hyperplasia if the calculated proportion of free PSA to total PSA is equal to or greater than about 25%.

* * * * *